United States Patent [19]

Florack

[11] 4,238,321
[45] Dec. 9, 1980

[54] PROCESS FOR THE SEPARATION OF STRAIGHT PARAFFINS FROM MIXED PARAFFINS

[75] Inventor: Petrus M. Florack, The Hague, Netherlands

[73] Assignee: Shell Oil Company, Houston, Tex.

[21] Appl. No.: 51,299

[22] Filed: Jun. 22, 1979

[30] Foreign Application Priority Data

Jun. 27, 1978 [NL] Netherlands .......................... 7806874

[51] Int. Cl.³ ............................................ C10G 25/03
[52] U.S. Cl. .................................. 208/310 Z; 585/826
[58] Field of Search ..................... 208/310 Z; 585/820, 585/826

[56] References Cited

U.S. PATENT DOCUMENTS

| | | | |
|---|---|---|---|
| 2,895,173 | 11/1958 | Hess et al. | 208/310 Z |
| 3,274,099 | 9/1966 | Broughton | 585/826 |
| 3,395,097 | 7/1968 | Senn | 208/310 Z |

*Primary Examiner*—Herbert Levine
*Attorney, Agent, or Firm*—Ronald R. Reper

[57] ABSTRACT

A process is disclosed for separation of straight chain paraffins from a mixture of paraffinic hydrocarbons by selective adsorption on a molecular sieve followed by desorption of the straight chain paraffins with gaseous hydrogen.

10 Claims, 1 Drawing Figure

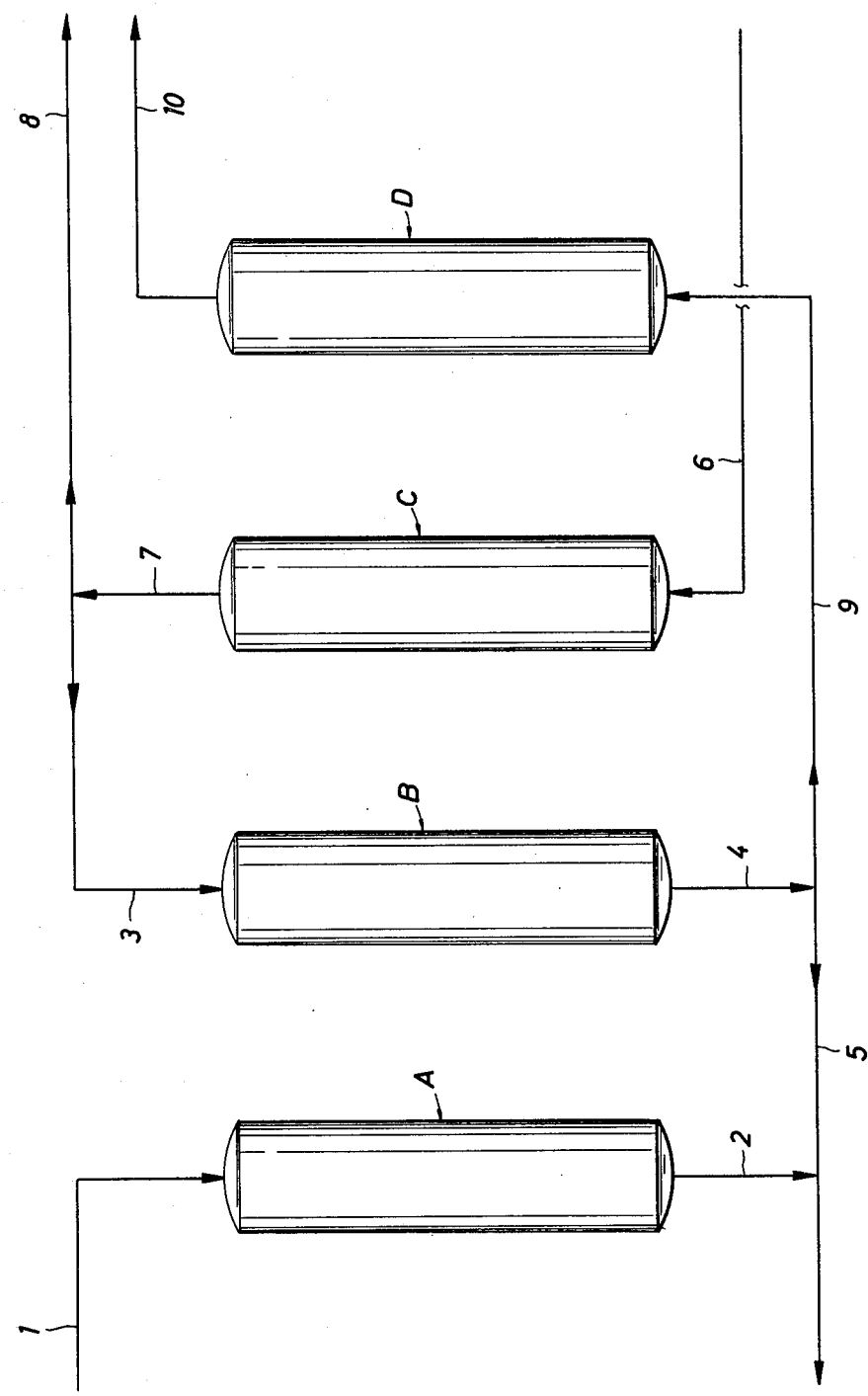

PROCESS FOR THE SEPARATION OF STRAIGHT PARAFFINS FROM MIXED PARAFFINS

BACKGROUND OF THE INVENTION

The inventin relates to a process for the separation of straight paraffins from a mixture mainly consisting of straight and branched paraffins (the feed) by selective adsorption of the straight paraffins on a molecular sieve, followed by desorption of the straight paraffins from the molecular sieve with the aid of hydrogen.

For use in gasolines, unbranched saturated non-cyclic aliphatic hydrocarbons (hereinafter called straight paraffins) are less suitable, because they have a lower octane number than branched saturated non-cyclic aliphatic hydrocarbons (hereinafter called branched paraffins) having the same number of carbon atoms. In order to prepare gasolines having a high octane number, methods have therefore been developed for the separation of the straight paraffins from a mixture containing straight and branched paraffins.

A known method to this end consists in passing a mixture mainly consisting of straight and branched paraffins (the feed) through a molecular sieve bed, which sieve adsorbs the straight but not the branched paraffins. When the molecular sieve is sufficiently loaded with straight paraffins (this will generally be shortly before the point at which not all straight paraffins would be adsorbed from the feed) the supply of feed is interrupted and hydrogen is passed through the molecular sieve bed in order to desorb the straight paraffins.

In the operation of this process a number of difficulties arise. When the supply of feed is replaced by counter-current hydrogen supply for the desorption of the straight paraffins the feed still present in the voids in the bed will be expelled by the hydrogen, and leave the bed together with the desorbed straight paraffins. This of course leads to a loss of capacity of the whole plant, because part of the supplied feed leaves the bed again in unpurified state. For that reason, after the desired quantity of straight paraffins has been absorbed, a co-purge step is employed, in which the supply of feed is replaced by supply of a mixture of hydrogen and straight paraffins, which mixture is passed through the molecular sieve bed in the same direction as the feed. The straight paraffins still present in the feed are adsorbed in the last part of the bed, and branched paraffins leave the bed. When all the branched paraffins have been expelled, the bed is fully filled with a mixture of hydrogen and straight paraffins, which latter may be adsorbed or non-adsorbed. Desorption of straight paraffins can now be effected by passing hydrogen through the bed counter-currently to the direction of the co-purge (and therefore of the feed).

Here again, problems are encountered which differ according to whether the feed is passed through the bed downwardly or upwardly.

If the feed is passed downwardly through the bed, the latter is charged with hydrogen after the preceding regeneration. Because the feed has a considerably higher specific gravity than hydrogen, channeling occurs during the passage through the bed, as a result of which the hydrogen is not expelled to a sufficient degree from the voids in the bed. Consequently optimum contact of the feed with the surface of the molecular sieve in the bed does not take place, as a result of which not all sites available on the molecular sieve for the adsorption of straight paraffin adsorption are utilized and the total amount of straight paraffins adsorbed remains far below the possible and desired level.

If the feed is passed upwardly through the bed and the co-purge (which consists of a mixture of hydrogen and straight paraffins) as well, the co-purge gas, which has a lower specific gravity than the feed (and also than the branched paraffins therein) finds the shortest way to the top, as a result of which channeling takes place and the feed or the branched paraffins therefrom are not expelled from the bed in an adequate manner. Another known method is described in British Pat. No. 1,067,171 which employs pressure reduction rather than introduction of a gas stream for co-purge and desorption.

The invention provides a process in which the aforementioned problems do not occur.

SUMMARY OF THE INVENTION

The invention therefore relates to a process for the separation of straight paraffins from a mixture mainly consisting of straight and branched paraffins (the feed) by selective adsorption of the straight paraffins on a molecular sieve with the aid of hydrogen, which process comprises consecutively (a) passing the feed downwardly through a molecular sieve bed which contains substantially no straight paraffins and the voids of which bed contain branched paraffins, until a desired quantity of straight paraffins has been adsorbed on the molecular sieve, (b) passing a mixture of straight paraffins and hydrogen downwardly through the molecular sieve bed until substantially all the branched paraffins have been expelled therefrom, (c) passing hydrogen upwardly through the molecular sieve bed until most of the straight paraffins have been desorbed and removed with the gas stream, and (d) passing branched paraffins upwardly through the molecular sieve bed until substantially all the hydrogen has been expelled therefrom.

BRIEF DESCRIPTION OF THE DRAWING

The drawing is a diagrammatic embodiment of apparatus suitable for carrying out continuously the process of the invention.

DESCRIPTION OF PREFERRED EMBODIMENTS

The process according to the invention is generally carried out in such a way that the temperature in steps (a), (b), (c) and (d) is substantially the same. The temperature is very suitably from 200° to 400° C., and the materials supplied to the beds are made in the vapor phase. To this end the feed and if necessary the other materials supplied are brought to the desired temperature in advance of contacting the molecular sieve bed.

The pressure in steps (a), (b), (c) and (d) is also very suitably substantially the same; it is preferably in the range from 5 to 50 bar.

Very suitably, feeds are used which consist of hydrocarbons with 5 and/or 6 carbon atoms. Although the feed consists mainly of straight and branched paraffins, it may also contain unsaturated and/or cyclical hydrocarbons (such as for example cyclopentane, methylcyclopentane, benzene) in minor quantities without having any adverse effect on the process according to the invention.

The molecular sieve must be selective, i.e. it must be capable of adsorbing straight paraffins and not branched paraffins. This selec-selectivity is dependent on the pore diameter of the molecular sieve. Very suitably the pore diameter is in the range from 0.4 to 0.6 nm.

The hydrogen to be used need not be completely pure and it may for example consist of gas having at least about 70% mol purity, and preferably at least 80% mol, originating from a reforming unit. The hydrogen may contain minor quantities of other substances, provided that they do not react with substances present in the feed or are adsorbed selectively relative to straight paraffins on the molecular sieve.

In step (a) the feed is preferably passed through the molecular sieve bed for such a time that at the end of the step the quantity of adsorbed straight paraffin is from 70 to 80% of the maximum quantity adsorbable by the bed. This leaves some adsorption capacity for the non-adsorbed straight paraffins which are still present in the bed and which are to be adsorbed in step (b), so that in that step a product is obtained which is free or substantially free of straight paraffins.

In step (b) a mixture of straight paraffins and hydrogen is passed through the bed. For this purpose use is very suitably made of part of the mixture becoming available in step (c).

For the branched paraffins passed through the bed in step (d) use may very suitably be made of part of the product (which consists largely or entirely of branched paraffins) leaving the molecular sieve bed in step (a).

The process according to the invention is advantageously combined with a process for the isomerization of straight paraffins into branched paraffins, which isomerization is very suitably carried out in the presence of hydrogen with the aid of a platinum-containing catalyst. Very suitable catalysts are those consisting of platinum on mordenite as carrier, for example as described in the U.S. Pat. No. 3,190,939. It is especially advantageous for the hydrogen becoming available in such an isomerization process after the paraffins have been removed therefrom, to be heated and to be used in step (c) of the process according to this invention.

If the process according to the invention is combined with a process for the isomerization of straight paraffins, the straight paraffins which become available in step (c) (and which are already mixed with hydrogen) can be very suitably isomerized. The non-converted straight paraffins which are still present in the mixture becoming available after the isomerization can again be separted according to the process of the invention, and so on. In this way all the straight paraffins present in a feed can be removed, and in so far as they are not converted into by-products (for example by cracking), they can be converted into branched paraffins.

Of course, the process according to the invention need not be carried out with the use of only one molecular sieve bed. Use is very suitably made of four or more beds arranged in parallel, in each of which the four steps are carried out consecutively, while the supply and discharge of the gas streams is regulated in such a way that at any given moment one of the four steps is being carried out in at least one bed. In this way the process according to the invention becomes essentially a continuous process.

The invention is elucidated with reference to the attached diagrammatic FIGURE. In the FIGURE, A, B, C and D represent four separate adsorbers, each charged with a molecular sieve bed. To adsorber A a mixture substantially consisting of paraffins with 5 to 6 carbon atoms is supplied as feed through a line 1. In the adsorber A, the straight paraffins are removed from said feed by adsorption on the molecular sieve, and the product, mainly consisting of branched paraffins, is removed through a line 2. The supply of feed is continued until approximately 75% of the maximum quantity of straight paraffins which can be adsorbed by the bed of adsorber A has been adsorbed, whereupon the supply of feed is stopped. At the same time, a mixture of straight paraffins and hydrogen is supplied through a line 3 to the adsorber B, in which the treatment is described for adsorber A has just been completed, until all the branched paraffins have been removed through a line 4. Lines 4 and 2 exit into in a common line 5. At the same time hydrogen is supplied through a line 6 to the adsorber C, in which the treatment as described for the adsorber B has just been completed, and through a line 7 a mixture of hydrogen and straight paraffins is removed from the system through a line 8. At the same time branched paraffins originating from the line 5 are supplied through a line 9 to the adsorber D, in which the treatment as described for the adsorber C has just been completed, until all the hydrogen has been expelled through a line 10. Subsequently, the above-mentioned treatments are repeated, but now in that adsorber which precedes the adsorber for which the corresponding treatment is described above. (D precedes A).

For each adsorber, only those lines are shown which were required for the description; it will be clear that each adsorber is provided with supply and discharge lines for all the streams described.

What is claimed is:

1. A process for the separation of straight paraffins from a feed mixture mainly consisting of straight and branched paraffins by selective adsorption of the straight paraffins on a molecular sieve, followed by desorption of the straight paraffins from the molecular sieve with the aid of hydrogen, which comprises consecutively
   (a) passing the feed downwardly through a molecular sieve bed which contains substantially no straight paraffins and the voids of which bed contain branched paraffins, until a desired quantity of straight paraffins has been adsorbed on the molecular sieve,
   (b) passing a mixture of straight paraffins and hydrogen downwardly through the molecular sieve bed until substantially all the branched paraffins have been expelled therefrom,
   (c) passing hydrogen upwardly through the molecular sieve bed until most of the straight paraffins have been desorbed and removed with the gas stream, and
   (d) passing branched paraffins upwardly through the molecular sieve bed until substantially all the hydrogen has been expelled therefrom.

2. A process as in claim 1, wherein steps (a), (b), (c) and (d) are carried out at substantially the same temperature.

3. A process as in claim 2, wherein the temperature is from 200° to 400° C.

4. A process as in claim 1, wherein steps (a), (b), (c) and (d) are carried out at substantially the same pressure.

5. A process as in claim 4, wherein the pressure is from 5 to 50 bar.

6. A process as in claim 1, wherein the feed mixture consists of hydrocarbons of 5 and/or 6 carbon atoms.

7. A process as in claim 1, wherein the molecular sieve has a pore diameter of 0.4 to 0.6 nm.

8. A process as in claim 1 wherein at the end of step (a) the quantity of adsorbed straight paraffins is from 70 to 80% of the maximum adsorbable amount.

9. A continuous process as in claim 1, wherein part of the product mixture from step (c) is recycled as feed to step (b).

10. A continuous process as in claim 1, wherein a part of the product leaving the molecular sieve bed in step (a) is used as part of the branched paraffin feed to step (d).

* * * * *